United States Patent [19]

Young

[11] Patent Number: 4,520,813
[45] Date of Patent: Jun. 4, 1985

[54] ENDOTRACHEAL TUBE HOLDER

[76] Inventor: Michael S. Young, 673 Dream Island Rd., Longboat Key, Fla. 33548

[21] Appl. No.: 542,444

[22] Filed: Oct. 17, 1983

[51] Int. Cl.³ .......................................... A61M 25/02
[52] U.S. Cl. ...................... 128/207.17; 128/DIG. 26; 604/179; 24/370; 24/230.5 AD; 24/230.5 TP; 24/265 H
[58] Field of Search .................. 128/207.17, DIG. 26; 604/174, 179, 180; 24/370, 230.5 AD, 230.5 TP, 265 H, 576, 578, 579, 688, 303, 129 R

[56] References Cited

U.S. PATENT DOCUMENTS

| | | | |
|---|---|---|---|
| 2,059,825 | 11/1936 | Talbott | 24/265 H |
| 3,286,713 | 11/1966 | Kurtz et al. | 604/180 |
| 3,602,227 | 8/1971 | Andrew . | |
| 3,648,703 | 3/1972 | Manker . | |
| 3,760,811 | 9/1973 | Andrew . | |
| 3,987,798 | 10/1976 | McGinnis . | |
| 4,270,529 | 6/1981 | Muto . | |
| 4,326,515 | 4/1982 | Shaffer et al. . | |
| 4,331,143 | 5/1982 | Foster . | |
| 4,331,144 | 5/1982 | Wapner . | |

FOREIGN PATENT DOCUMENTS 1943 of 1870 United Kingdom .................. 24/579

OTHER PUBLICATIONS

Instructions, Olympic Endo-Lok, Olympic Medical Corp, (Undated).
Packaging Insert, Hudson Model No. 1065, Disposable Endotracheal Tube Holder, Hudson Oxygen Therapy Sales Co. (10-80).

Primary Examiner—Henry J. Recla
Attorney, Agent, or Firm—Benjamin P. Reese, II

[57] ABSTRACT

An endotracheal tube holder which is particularly suitable for use during medical emergency situations. The holder comprises a pair of identical curved, plate-like hooking members and an interconnecting attachment band which encircles the patient's face and neck. Each of the hooking members has a dogleg opening for receiving and engaging the endotracheal tube when the hooking members are overlapped in position over the patient's mouth. The attachment band has segments of bristly fastening material of the type commercially available under the Velcro trademark which enable adjustment of its length to accommodate patient's of various sizes.

7 Claims, 5 Drawing Figures

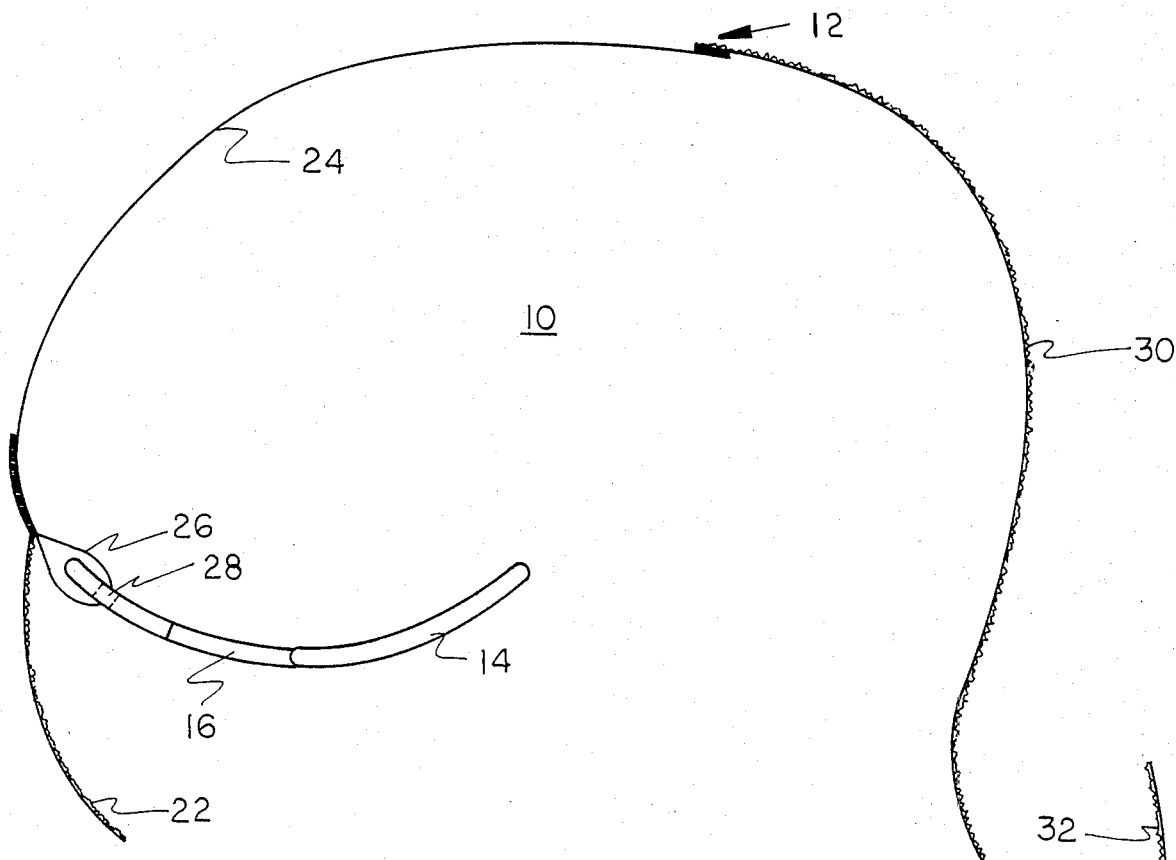
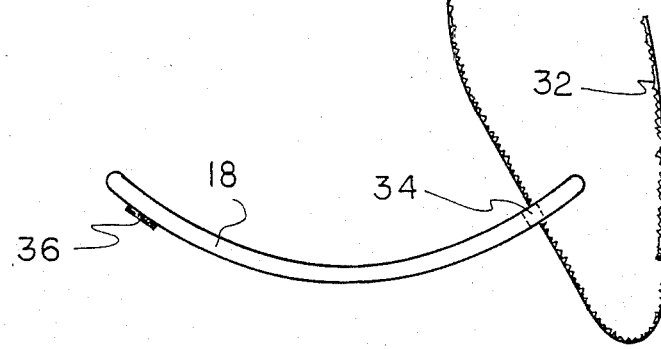
FIG. 3
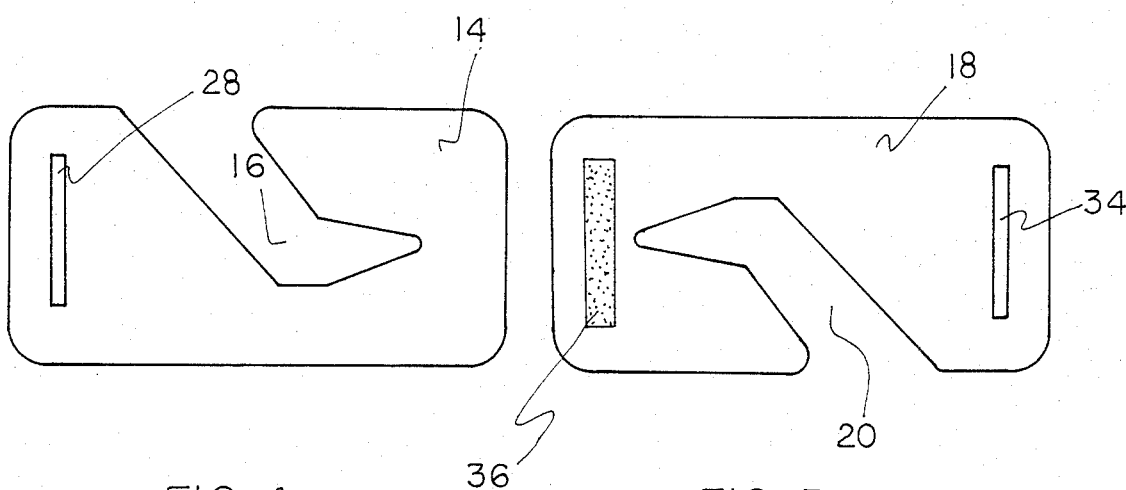
FIG. 4      FIG. 5

ENDOTRACHEAL TUBE HOLDER

BACKGROUND OF THE INVENTION

This invention relates to a new and improved endotracheal tube holder which is particularly suitable for use during medical emergency situations.

During medical emergency situations, it is often necessary to provide an unobstructed passageway or airway to the patient's lungs to administer oxygen or to facilitate breathing. The need to provide an unobstructed passageway or airway is particularly acute during medical emergency situations involving blockage of the patient's mouth, throat or trachea by blood, mucus or other foreign material. An unobstructed passageway or airway is commonly provided in such situations by insertion of an endotracheal tube through the patient's mouth and into the trachea to a point below the vocal cords but above the bronchial tubes. It is most important that the tube be securely maintained in this position during the entire period of its use to avoid possible asphyxiation or damage to the trachea, vocal cords and bronchial tubes.

A common and typical means for maintaining an endotracheal tube in the above described position is to attach the exposed end of the tube to the patient's face with adhesive tape. Unfortunately, there are several serious disadvantages which are inherent in the use of such means for maintaining an endotracheal tube in position. First, since a significant amount of tape is often required, even a well-trained person will usually take an excessive amount of time in taping the tube in position during medical emergency situations. Furthermore, as it absorbs perspiration, saliva, blood or other fluids, the adhesive tape will often loosen and allow the tube to be accidentally displaced. And, of course, it is not possible to use tape to attach the tube to the patient's face in many medical emergency situations, such as those including facial bleeding, facial burns or the like.

The prior art provides several endotracheal tube holders and the like which were apparently developed to overcome the above described and other disadvantages inherent in taping the tube to the patient's face. Certain of the prior art endotracheal tube holders successfully overcome one or more of such disadvantages, such as the problems which occur when the adhesive tape loosens during the period of use of an endotracheal tube which is taped to the patient's face. However, it is not believed that any of the prior art endotracheal tube holders are particularly suitable for use during medical emergency situations. In that regard, it is believed that the structures and methods of use of most prior art endotracheal tube holders are too complex for even a well-trained person to secure the tube in position without taking an excessive amount of time during many medical emergency situations. It is desirable to have an endotracheal tube holder which not only securely maintains the tube in position during the entire period of its use but also is sufficiently simple in its structure and method of use for even a poorly trained person to rapidly secure the tube in position during life or death situations, such as those often encountered by paramedical personnel working outside a hospital environment.

SUMMARY OF THE INVENTION

The present invention provides a new and improved endotracheal tube holder which is particularly suitable for use during medical emergency situations.

The endotracheal tube holder of the present invention comprises a pair of identical, curved plate-like hooking members and a face and neck encircling attachment band interconnecting those hooking members. Each of the hooking members has a dogleg opening which becomes progressively smaller when moving inward from its mouth for receiving and engaging the same endotracheal tube. The dogleg openings are opposed while receiving and engaging the tube when the attachment band encircles the patient's face and neck.

The attachment band of the endotracheal tube holder of the present invention is formed from four separate and distinct segments, i.e. a first short strip of hooked bristly fastening material, a longer strip of elastic material, a still longer strip of looped bristly fastening material and a second short strip of hooked bristly fastening material, which are permanently connected or joined. One of the hooking members is permanently but moveably connected to the strip of elastic material near the connection or joint between the first strip of bristly fastening material and the strip of elastic material by means of a loop in the elastic material passed through a slot in the hooking member. The other hooking member is adjustably and removeably connected to the strip of looped bristly fastening material by passing the second strip of hooked bristly fastening material and strip of looped bristly fastening material through a slot in the hooking member and folding the second strip of hooked bristly fastening material onto the strip of looped bristly fastening material. This hooking member has a strip of looped bristly fastening material attached to its surface near the end opposite to its slot for adjustable and removeable connection of the first strip of hooked bristly fastening material.

These and many other advantages, features and objects of the present invention will be apparent from the following Brief Description of the Drawings, Detailed Description of the Preferred Embodiment and Claims, and the accompanying Drawings.

BRIEF DESCRIPTION OF THE DRAWINGS

FIG. 3 is a top plan view of the endotracheal tube holder shown in FIG. 1.

FIG. 4 is a front elevational view of the hooking member shown on the left in FIG. 3.

FIG. 5 is a front elevational view of the hooking member shown on the right in FIG. 3.

DETAILED DESCRIPTION OF THE PREFERRED EMBODIMENT

The preferred embodiment of the endotracheal tube holder of the present invention is illustrated in FIGS. 1-5.

Figure 1:
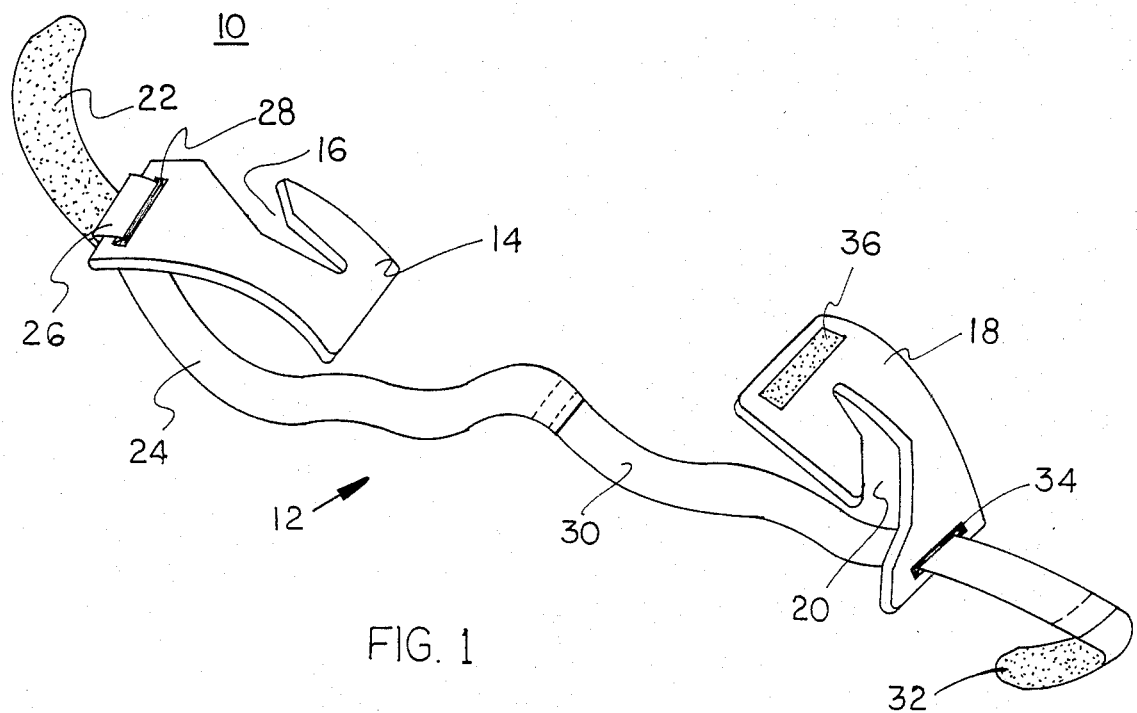
FIG. 1 is a general perspective view of the preferred embodiment of the endotracheal tube holder of the present invention.
Figure 2:
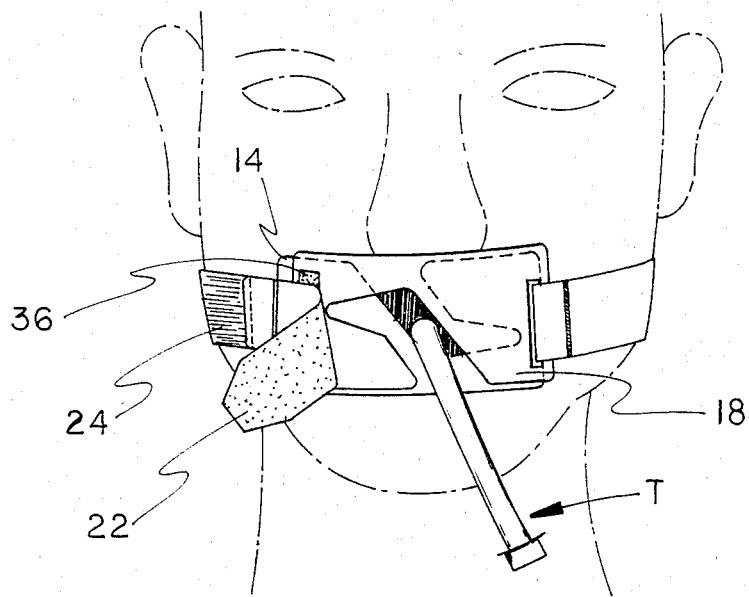
FIG. 2 is a front elevational view of the endotracheal tube holder shown in FIG. 1 positioned on a patient to securely maintain an endotracheal tube in its proper position.

Referring to FIGS. 1-3, the endotracheal tube holder 10 which is illustrated comprises a face and neck encircling attachment band 12 interconnecting a first curved, plate-like hooking member 14 having a dogleg opening 16 for receiving and engaging an endotracheal tube and a second curved, plate-like hooking member 18 having a dogleg opening 20 for receiving and engaging the same endotracheal tube. The hooking members 14 and 18 are identically shaped but are positioned relative to each other on the opposite ends of the attachment band 12 such that their respective dogleg openings 16 and 20 are opposed while receiving and engaging the tube when the attachment band 12 encircles the patient's face and neck in the manner illustrated in FIG. 2. Preferrably, each of the hooking members 14 and 18 is formed as a one-piece molded, clear plastic body.

As best illustrated in FIGS. 1 and 3, the attachment band 12 is formed from four separate and distinct segments which are permanently connected or joined by sewing or other conventional means. From left to right in FIGS. 1 and 3, one end of a first short strip 22 of hooked bristly fastening material of the type commercially available under the Velcro trademark is permanently connected or joined to one end of a longer strip 24 of latex or another similar elastic material. The same end of the strip 24 is permanently but moveably connected to the hooking member 14 by means of a loop 26 in the strip 24 which is passed through a slot 28 in the hooking member 14. The other end of the strip 24 is permanently connected or joined to a still longer strip 30 of looped bristly fastening material of the type commercially available under the Velcro trademark. The other end of the strip 30 is permanently connected or joined to one end of a second short strip 32 of hooked bristly fastening material of the type commercially available under the Velcro trademark.

As best illustrated in FIG. 3, the strips 30 and 32 are connected or joined with their bristly fastening surfaces facing in the same direction. This facilitates adjustable and removeable connection of the hooking member 18 to the strip 30 by passing the connected or joined strips 32 and 30 through the slot 34 in the hooking member 18 and folding the strip 32 onto the strip 30 such that their bristly hooks and loops engage each other in the usual manner. The hooking member 18 has a strip 36 of looped bristly fastening material of the type commercially available under the Velcro trademark permanently attached on its surface near its end opposite the slot 34 by glueing or other conventional means. This facilitates adjustable and removable connection of the strip 22 to the hooking member 18 when positioning the attachment band 12 around the patient's face and neck as illustrated in FIG. 2.

As best illustrated in FIGS. 4 and 5, each of the dogleg openings 16 and 20 in the hooking elements 14 and 18 becomes progressively smaller in size when moving inward from its mouth. Referring to FIG. 2, it will be readily appreciated that this permits the opposed, dogleg openings 16 and 20 to receive and engage endotracheal tubes of various sizes. Thus, by appropriate sizing, it is possible to use the endotracheal tube holder 10 with the smallest pediatric tubes to the largest adult tubes which are commercially available. Furthermore, as best illustrated in FIGS. 2 and 3, each of the hooking elements 14 and 18 has a radius of curvature which enables it to conform comfortably to patient's faces of many different shapes and sizes.

Having described the structure of the endotracheal tube holder 10, its use will now be described. Referring to FIGS. 1 and 3, prior to the occurrence of a medical emergency situation, the hooking element 18 is connected to the appropriate end of the attachment band 12 with the length of the attachment band 12 adjusted in the manner described above to accommodate a patient of average size. During a medical emergency situation, the patient is first intubated in the customary and usual manner. Following intubation, the first hooking element 14 is placed over the patient's mouth with its dogleg opening 16 engaging the endotracheal tube T in the manner illustrated in FIG. 2. Then, the attachment band 12 is pulled around the patient's face and neck and the second hooking element 18 placed over the patient's mouth with its dogleg opening 20 engaging the endotracheal tube T in the manner illustrated in FIG. 2. Finally, the hooked bristly surface of the strip 22 is pressed onto the looped bristly surface of the strip 36 to appropriately secure the attachment band 12 around the patient's face and neck. Of course, the length of the attachment band 12 can be adjusted in the manner described above if the patient is not of average size.

While the present invention has been disclosed in connection with its preferred embodiment, it should be understood that there may be other embodiments which fall within the spirit and scope of the invention as defined by the following claims.

I claim:

1. An endotraceal tube holder, comprising a pair of identical curved, plate-like hooking members adapted to overlie one another and each having first and second opposite ends and first and second opposite sides, one of said hooking members having a dogleg opening extending inwardly from said first side thereof toward said first end thereof, the other of said hooking members having a dogleg opening extending inwardly from said second side thereof toward said first end thereof whereby, when said holder is used, said openings receive and engage the same endotracheal tube, and a face and neck encircling attachment band connected to said ends of each of said hooking members.

2. An endotracheal tube holder as recited in claim 1, wherein each of said dogleg openings becomes progressively smaller in size when moving inward from its mouth.

3. An endotracheal tube holder as recited in claim 1, wherein each of said hooking members is a one-piece, molded, clear plastic body.

4. An endotracheal tube holder as recited in claim 1, wherein said attachment band comprises a first strip of hooked bristly fastening material, a strip of elastic material, a strip of looped bristly fastening material, and a second strip of hooked bristly fastening material, one end of said first strip of hooked bristly fastening material being permanently connected or joined to one end of said elastic material, the other end of said strip of elastic material being permanently connected or joined to one end of said strip of looped bristly fastening material, and the other end of said strip of looped bristly fastening material being permanently connected or joined to one end of said second strip of hooked bristly fastening material such that their respective bristly fastening surfaces face in the same direction.

5. An endotracheal tube holder as recited in claim 4, wherein said end of said strip of elastic material permanently connected or joined to said end of said first strip of hooked bristly fastening material is permanently but moveably connected to one of said hooking members by means of a loop in said strip of said elastic material passed through a slot in said hooking member.

6. An endotracheal tube holder as recited in claim 4, wherein one of said hooking members is adjustably and removeably connected to said strip of looped bristly fastening material by passing said second strip of hooked bristly fastening material and said strip of looped bristly fastening material through a slot in said hooking member and folding said second strip of hooked bristly fastening material onto said strip of looped bristly fastening material.

7. An endotracheal tube holder as recited in claim 6, wherein said hooking member which is adjustably and removeably connected to said strip of looped bristly fastening material has a strip of looped bristly fastening material permanently attached to its surface near its end opposite to said slot for adjustable and removeable connection of said first strip of hooked bristly fastening material when said attachment band is positioned around the patient's face and neck.

* * * * *